United States Patent
Kinnunen

(10) Patent No.: US 8,781,564 B2
(45) Date of Patent: Jul. 15, 2014

(54) METHOD AND APPARATUS IN CONNECTION WITH EXERCISE

(75) Inventor: Hannu Kinnunen, Oulu (FI)

(73) Assignee: Polar Electro Oy, Kempele (FI)

(*) Notice: Subject to any disclaimer, the term of this patent is extended or adjusted under 35 U.S.C. 154(b) by 419 days.

(21) Appl. No.: 12/994,185

(22) PCT Filed: Jun. 2, 2008

(86) PCT No.: PCT/FI2008/050318
§ 371 (c)(1),
(2), (4) Date: Nov. 23, 2010

(87) PCT Pub. No.: WO2009/147279
PCT Pub. Date: Dec. 10, 2009

(65) Prior Publication Data
US 2011/0137191 A1    Jun. 9, 2011

(51) Int. Cl.
*A61B 5/0402*    (2006.01)
(52) U.S. Cl.
USPC .......................... 600/512; 600/508; 600/509
(58) Field of Classification Search
CPC ........... A61B 5/04011; A63B 24/0062; A63B 2230/04
USPC .......................... 600/508, 509, 514, 519, 512
See application file for complete search history.

(56) References Cited

U.S. PATENT DOCUMENTS

| | | | | |
|---|---|---|---|---|
| 4,106,495 A * | 8/1978 | Kennedy | ........................ | 600/512 |
| 4,136,690 A * | 1/1979 | Anderson et al. | ............. | 600/512 |
| 5,803,084 A | 9/1998 | Olson | | |
| 6,038,469 A * | 3/2000 | Karlsson et al. | ............. | 600/512 |
| 2005/0209525 A1 | 9/2005 | Bojovic et al. | | |

FOREIGN PATENT DOCUMENTS

RU        2118117 C1    8/1998
WO    WO2008026073 A2    3/2008

OTHER PUBLICATIONS

International Search Report and Written Opinion for corresponding International Application No. PCT/FI2008/050318, pp. 1-9, Tuomo Reiniaho, Feb. 26, 2009.

* cited by examiner

*Primary Examiner* — Joseph Stoklosa
(74) *Attorney, Agent, or Firm* — Hoffmann & Baron, LLP

(57) ABSTRACT

An apparatus in connection with a fitness exercise of a person, including means for processing multidimensional electrocardiographic data of the person, the multidimensional electrocardiographic data comprising at least two spatially separately measured electrocardiographic signal components, means for forming a vectorcardiographic measure on the basis of the multidimensional electrocardiographic data, and means for applying the vectorcardiographic measure in determination of a fitness exercise related parameter.

21 Claims, 5 Drawing Sheets

US 8,781,564 B2

METHOD AND APPARATUS IN CONNECTION WITH EXERCISE

CROSS-REFERENCE TO RELATED APPLICATION

This application is a National Phase application of International Application No. PCT/FI2008/050318, filed Jun. 2, 2008, which is incorporated herein by reference.

BACKGROUND

1. Field

The disclosure relates to sports, particularly to fitness exercises.

2. Description of the Related Art

Heart rate is often used as a measure of the exertion level of a person in a fitness exercise. However, in some circumstances, the heart rate does not apply as a true indicator of stress level of an exercise. That is, in some cases a high heart rate, for instance, is not an indication of high work rate of the person.

There is thus a need to provide an improved way of determining the exertion level of a fitness exercise on a person.

SUMMARY

In an aspect, there is provided an apparatus in connection with a fitness exercise of a person. The apparatus comprises means for processing multidimensional electrocardiographic data of the person, the multidimensional electrocardiographic data comprising at least two spatially separately measured electrocardiographic signal components, means for forming a vectorcardiographic measure on the basis of the multidimensional electrocardiographic data, and means for applying the vectorcardiographic measure in determination of a fitness-exercise-related parameter.

In another aspect, there is provided a method in connection with a fitness exercise of a person. The method comprises processing multidimensional electrocardiographic data of the person, the multidimensional electrocardiographic data comprising at least two spatially separately measured electrocardiographic signal components, forming a vectorcardiographic measure on the basis of the multidimensional electrocardiographic data, and applying the vectorcardiographic measure in determination of a fitness-exercise-related parameter.

BRIEF DESCRIPTION OF THE DRAWINGS

In the following the invention will be described in greater detail by means of preferred embodiments with reference to the accompanying drawings, in which FIG. 1 highlights installation of electrodes on a person carrying out a fitness exercise.

DETAILED DESCRIPTION

Figure 1:
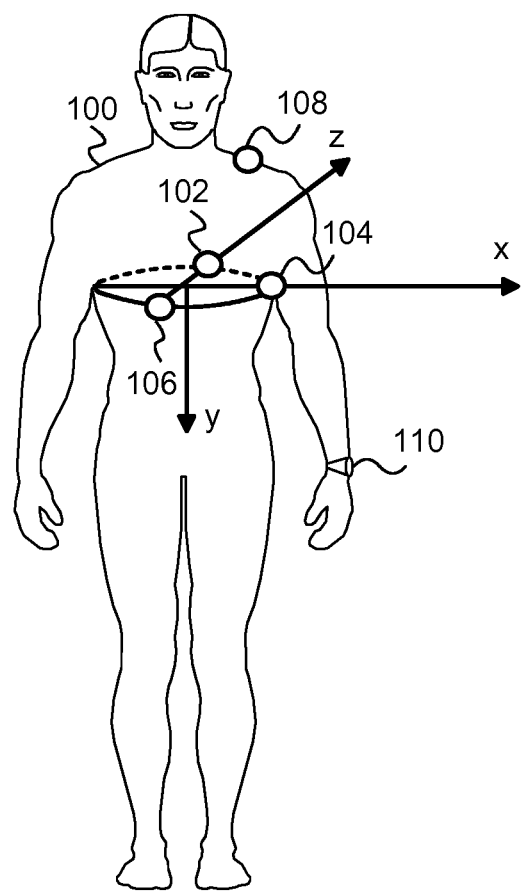

FIG. 1 shows one example of measurement of multidimensional electrocardiographic data from a person 100 relating to a fitness exercise. The measured data may be processed during and/or after the exercise. The electrocardiographic data measured from the person is expected to be illustrative of data measured from a healthy person having no heart disorders, for instance. An ECG (Electrocardiogram) is a recording of the changes in electrical potentials between different sites on the skin and arises from the periodic activity of the cardiac musculature. The ECG reflects the depolarization and repolarization events connected with cardiac excitation and conduction. However, an ECG does not provide direct information about the contraction and pumping efficiency of the heart.

An ECG curve describes the migration of the excitatory front on the myocardium. Each deflection originates from the propagating depolarization or repolarization fronts in different parts of the cardiac muscle. The ECG represents the superposition of the depolarization and repolarization on different sites of the heart.

A first deflection in the normal ECG is a P wave representing atrial depolarization. The wave for atrial repolarization is masked by the succeeding waves. Q, R and S waves together constitute a QRS-complex which represents ventricular depolarization. In the QRS complex, every initial negative deflection is denoted by Q, every positive deflection by R, and every negative deflection that follows R, by S. The QRS complex is succeeded by a T wave which reflects repolarization of the ventricles.

Activation of the ventricular muscle takes place from endocardium to epicardium and from the apex of the ventricles to the base. The depolarization of the ventricle is almost simultaneous in the entire ventricular musculature causing a steep R wave, whereas the duration of the repolarization phase in different parts of the ventricles vary resulting in a less steep T wave. In most leads, the T wave is deflected in the same direction from the isoelectric line as the major component of the QRS complex. This indicates that the repolarization process proceeds in a direction counter to the depolarization process. By using several ECG leads for measuring several ECG signal components, and by following changes especially in repolarization phase, it is possible to gain information about the contraction and pumping efficiency of the heart.

In rest, the T wave is typically deflected in the same direction from the isoelectric line as the major component of the QRS complex which typically is the R component. In vectorcardiography, this leads to a situation where the QRS loop and the T loop are directed close to the same direction. In practice, this means that the activation of the ventricular muscle takes place from endocardium to epicardium and from the apex of the ventricles to the base, whereas the repolarization proceeds in the opposite direction. This situation enables optimal pumping efficiency. An explanation is that the center part of the epicardium is mechanically more elastic at the time when the apex contracts and therefore the emptying of the chambers, particularly that of the left chamber, is better.

During exercise, together with increased exercise intensity blood pressure rises remarkably, respiratory activity increases and the oxygen demand of heart muscle increases. As coronary arteries are located on the surface of the heart that is surrounded by the lungs, and are thus exposed to the pressure changes that take place with inhalation and expiration in the lungs, exercise affects the heart's oxygen supply and its pumping efficiency, particularly when intensity is close to maximum and/or when exercise duration is long.

Changes in the heart's oxygen need vs. supply are reflected in the repolarization period at that part of heart muscle. Also if there are changes in ion concentrations in the body fluids, they can be reflected particularly in the repolarization phase of heart cell activity. If repolarization is delayed in some part of the heart, it may adversely affect the following depolarization period as well. Local and small changes can negatively affect the heart's pumping efficiency even though they cannot be monitored with surface ECG. However, by combining the surface ECG information from several directions and following the changes it can be possible to detect such local and small changes that affect the heart's pumping efficiency. In one embodiment, the changes in the angle between the R loop and the T loop are followed. In another embodiment, the changed vectorcardiographic information are combined with the heart rate information, because some part of the information regarding the change is related to the heart rate information and some part of the information is related to contraction or pumping efficiency.

The person 100 depicted in FIG. 1 has four measurement electrodes 102 to 108 installed on him. The electrode 106 may be placed on the chest, the electrode 104 may be placed on the side, the electrode 102 may be placed on the back and the electrode 108 may be positioned on the shoulder of the person. ECG signal components of a multidimensional ECG data may be measured over each pair of electrodes. For instance, a first signal component may be measured by using a coupling of electrodes 102 and 104, a second signal component may be measured by a coupling of electrodes 102 and 106, and a third signal component may be measured by using a coupling of electrodes 104 and 106.

The multidimensional electrocardiographic data includes at least two spatially separated electrocardiographic signal components. The two spatially separated components are obtainable by using two of the couplings provided by at least three electrodes 102 to 106. The signal component in x direction may be extracted from each coupling signal and the extracted x signal components may be combined to a combination signal illustrative of the electrocardiographic signal in the x direction. The two other orthogonal directions y and z may be handled correspondingly.

The electrodes 102 to 106 may be positioned on the person such that they allow detection of signal components in orthogonal directions x, y and z depicted in the figure. In an embodiment, the electrodes 102 to 106 are positioned orthogonally with respect to each other that is each of them reside on one of the x, y and z axis. Alternatively, the electrodes 102 to 106 may be positioned non-orthogonally, and the orthogonal components x, y and z may be calculated from the measured signals. For instance, as the figure shows, the electrodes in the couplings 104-106 and 102-104 are positioned such that they allow detection of an electrocardiographic signal at least in x and z directions. To detect the y-component as well, the electrodes 102 to 106 may be placed at different heights of the person, so the back electrode 102 may be positioned higher on the person than the chest electrode 106, for instance. For effective detection of the y-component, instead of the electrode 104, the shoulder electrode 108 may be used.

Figure 2:
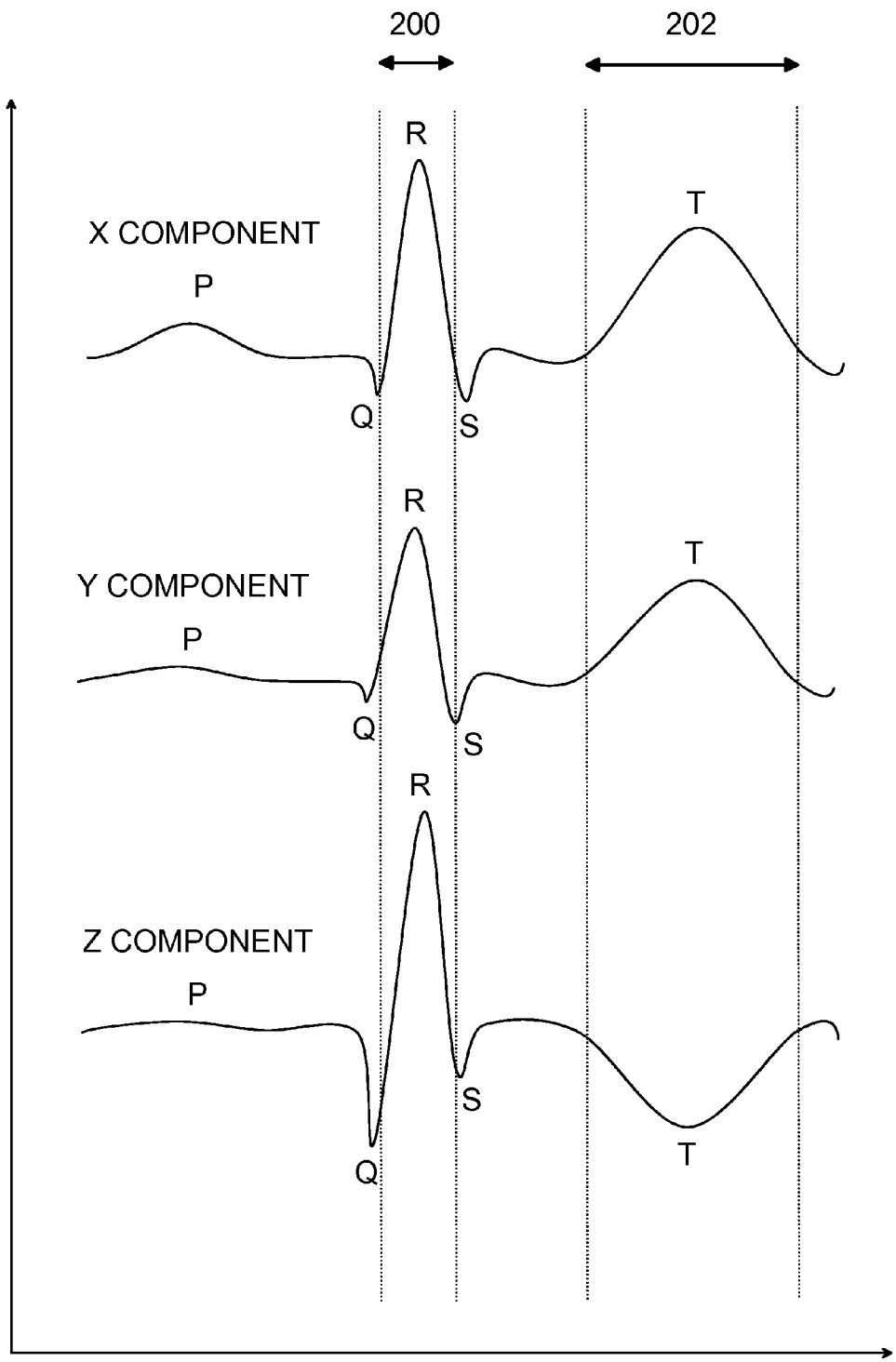
FIG. 2 illustrates ECG components in orthogonal directions.

FIG. 2 illustrates the electrocardiographic signal components in orthogonal directions x, y and z. The topmost graph illustrates the x-component, the y-component is depicted in the middle and the z-component at the bottom of the figure. Time windows of R and T waves are illustrated with reference numerals 200 and 202, respectively.

It may be seen that the time structure of the signal components measured in different directions may differ somewhat from each other. In the figure, the R peak in the z-component is higher than in the y-component and the T waves are inverse to each other, for instance.

Determination of the multidimensional ECG may be done in many ways from the signals measured by the pairs of electrodes. In one embodiment, the x components of all the couplings are combined, by averaging for example, to a combination x component. The y and z signals may be handled correspondingly. The combination x, y and z signals may then be combined to a combination multidimensional ECG.

Alternatively, multidimensional signals may be formed coupling-specifically, and the multidimensional coupling-specific signals may then be combined to a combination multidimensional signal, which may be presented as a vectorcardiographic representation. In this case, averaging may be used.

Figure 3:
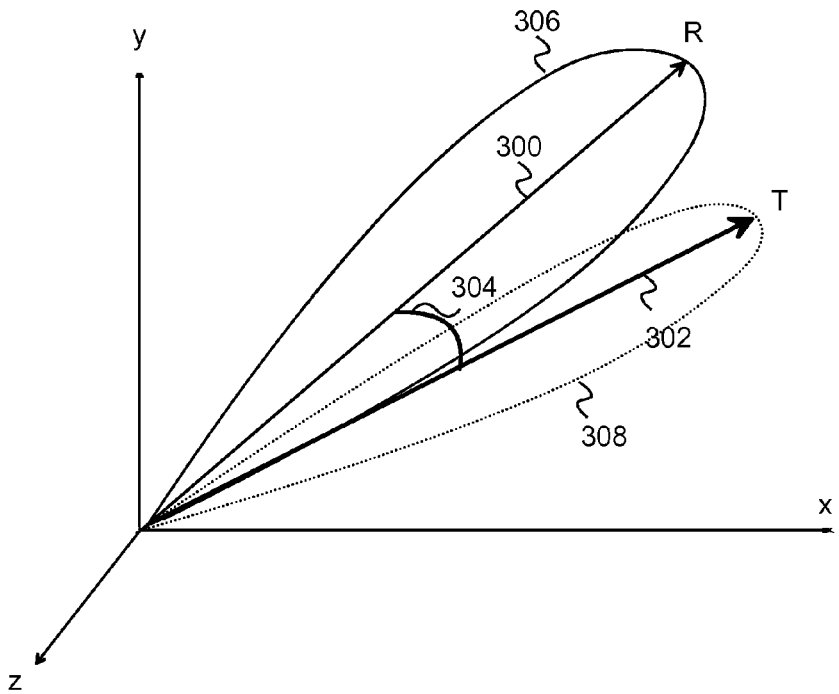
FIG. 3 highlights the time-dependent properties of a multidimensional ECG signal.

FIG. 3 shows a vectorcardiographic representation of two wave components. The R loop 306 is obtained by plotting the sampling points of x, y, z into a multidimensional coordinate system, wherein the sampling points are recorded during the R time window 200 illustrated in FIG. 2.

The T loop 308 is obtained by plotting the sampling points of x, y, z into a multidimensional coordinate system, wherein the sampling points are recorded during the T time window 202 of FIG. 2.

In an embodiment, a vector 300 between the origin and the furthest point from the origin is used for characterizing the R wave in the xyz coordinate system. Similarly, a vector 302 depicting the combination T wave may be provided by connecting a line between the origin and the outmost point of the loop 308. A vector measure between these two vectors 300, 302 may be determined. The vector measure may be the angle 304 between the combination R (300) and T (302) vectors, for instance. In an embodiment, the vector measure is TCRT (Total Cosine R to T). The vector measure may also be any other measure that can be determined from the relationship of the R and T vectors in the orthogonal coordinate space.

The amplitude/length and direction of the vectors representing the R and T waves may change over the time. In an embodiment, the vectors are updated continuously based on fifty previous heartbeats, for instance. Alternatively, the vectors may be updated only after a predetermined number of heartbeats has occurred or a predetermined time period has lapsed.

Figure 4:
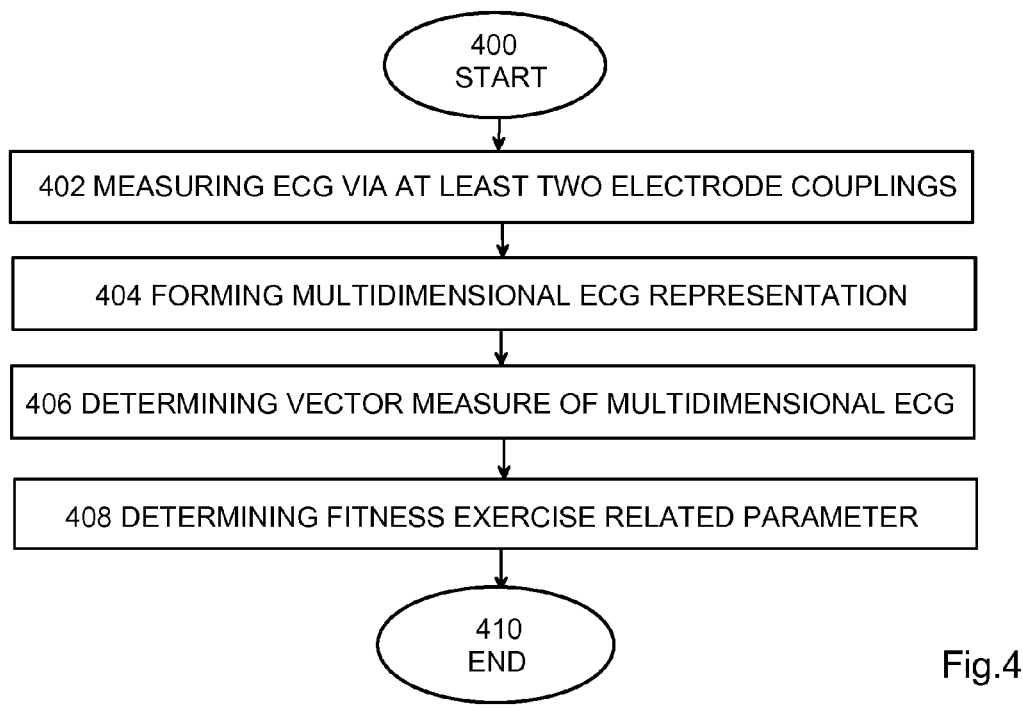
FIG. 4 shows an embodiment of a method.

FIG. 4 shows an embodiment of a method. The method may be applied in connection with a fitness exercise carried out by a healthy person having no heart disorders, for instance.

In 402, ECG is measured from the person by using at least two spatially separated electrode couplings. At least three electrodes 102 to 106 may be used for establishing the spatial separation of the couplings. If there are three electrodes 102 to 106 positioned in spatially different positions on the person, a first coupling may be between the first and second electrodes 102, 104, and the second coupling may be between the first and third electrodes 102, 106. In a first embodiment, the measurement on the couplings is simultaneous so that both signals on both couplings are measured all the time. In another embodiment, the measurement on the couplings is time-divided such that the measurement is carried out on the couplings alternately. In this case, it may be assumed that the measurement of the coupling not being measured is constant over the non-measurement period. We may assume an example where a first coupling and a second coupling are used. The first coupling is measured during a first time interval and the second coupling during a second time interval. During the second time interval, when the first coupling is not measured, the measurement results from the first coupling during the first time interval may be used in determining the multidimensional ECG, RT vectors and the vector measure.

In 404, a multidimensional ECG representation is formed from the signals measured in 402. The multidimensional representation here means a representation including at least three mutually different directions such that the directions are not in a plane. That is, the third direction is not in the plane determined by the two other directions. In an embodiment, the three directions are mutually orthogonal directions.

The multidimensional ECG is basically an ECG, where the signal components in mutually orthogonal directions x, y and z have been combined. In the multidimensional ECG, as in usual ECG, time windows representing the R wave and the T wave may be determined. The time window representing the R wave, for instance, may include upward and downward directing sections or predetermined length around the peak.

In an embodiment, a vectorcardiographic representation of the multidimensional ECG is provided. During a heart beat, that is during a PQRST cycle of the ECG, the vectorcardiographic presentation is a vector having time-varying characteristics in view of the amplitude and directions. With regard to the R peak, a curve representing sampling points of the multidimensional ECG signal during the R time window may be drawn. The vector representation of the R wave may correspond to a connecting line from the origin to the furthest point of the loaf. Similarly to a vector representing the R window, a vector representing the T window may be determined.

In 406, a vector measure is determined from the data formed in 404. As explained above, vectors representing R and T waves and varying in direction and magnitude over time is drawn. Each of these vectors may be averaged over time. The vectors may be averaged vectors of the latest 100 heart beats, for instance.

In an embodiment, the vector measure characterizes the relationship between the R and T vectors. The vector measure may be the angle between the R and T vectors or TCRT (Total Cosine R to T), for instance. Small TCRT may indicate high pumping efficiency of the heart. If the TCRT is high, the heart's pumping efficiency may be reduced. Small TCRT refers to the normal situation with normal depolarization and repolarization in all parts of heart. This can be linked to high pumping efficiency because of adequate filling of the ventricles, adequate oxygenation of heart cells (capillary flow), and proper ion concentrations in the heart cells.

In 408, a fitness-exercise-related parameter is determined on the basis of the vector measure formed in 406. The exercise-related parameter may be an exertion level or the energy consumption of the person in the fitness exercise. A large deviation between the R loop 306 and the T loop 308 may indicate smaller energy consumption than a small deviation with a constant heart rate.

The exercise-related parameter may also be an instruction indicating on which level the exercise could be started or continued. The conclusions are given in Table 1 below.

The parameter may also characterize mental stress of the person before or after the exercise. Alternatively, a capacity parameter of the person may be determined. The capacity parameter may indicate if the person is in a good or bad physical condition or if the plasma volume of the person is high.

The conclusions of 408 may be drawn up solely on the basis of the vector measure determined in 406. For instance, if TCRT is over a predetermined threshold value, this may be indicated to the person. A high TCRT may indicate to the person that training on that day should be light or that there should be no training at all.

TABLE 1

Instructions to the person in view of HR and TCRT values

| HR low | HR moderate | HR high |
|---|---|---|
| TCRT low person at rest/ well recovered HR corresponds to rest HR –> ok to start exercise | TCRT low good physical condition higher than normal plasma volume –> ok to continue exercise | TCRT low good physical condition higher than normal plasma volume –> ok to continue exercise |
| TCRT normal low exertion level HR corresponds to exertion level –> ok to exercise | TCRT normal HR corresponds to exertion level ok to continue exercise | TCRT normal HR corresponds to exertion level ok to continue exercise |
| TCRT high stress or overexertion on the person –> not advisable to start exercise | TCRT high HR too high compared to exertion level Heart pumping capacity lower than normal –> not optimal to continue exercising on current level | TCRT high HR too high compared to exertion level Heart pumping capacity lower than normal –> not optimal to continue exercising on current level |

Table 1 shows how the conclusions to control the exercise may be drawn solely on the basis of the vectorcardiographic measure. The first two rows indicate the situations where the TCRT is low or normal. Independent of the HR value, the low or normal value of the TCRT may be an indication that it is appropriate to start or continue an exercise.

However, if the TCRT value exceeds a predetermined threshold value, that is the limit between the "normal TCRT" and the "high TCRT", this is an indication that the heart's pumping efficiency is reduced. An indication may be given to the user either to stop the exercise or at least to reduce the stress of the exercise.

In another embodiment, the vector measure may be used together with a heart rate parameter, such as heart rate (HR), to provide instructions for the user in relation to the fitness exercise. Two or more categories for the heart rate may be provided, such as low, moderate and high heart rate. Furthermore, two or more categories for the vector measure, such as TCRT, may be provided. In an embodiment, the categories may be low, normal and high TCRT.

Before the exercise, if the heart rate is low and the TCRT is low/normal, it may be concluded that the person is not overstressed and a training exercise may be started.

If the TCRT is high despite the fact that the HR is low, this may indicate that the person is mentally or physically overstressed and should perhaps not consider starting a fitness exercise.

During the exercise, if the person has moderate HR and low TCRT, this may be an indication of high performance capability. It may be concluded that the exertion level of the exercise level is suitable for the person.

If the person has moderate HR and high TCRT, this may be an indication that the person is not fully fit to carry on with the exercise at that level. It may be that the person has not fully recovered from a previous exercise, for instance. This information may be communicated to the person.

If the person has high HR and low TCRT, this may be an indication of good physical condition of the person. If the HR is high and TCRT moderate, the HR corresponds to the person's exertion level and it is appropriate for the person to exercise at that HR level.

If the person has high HR and high TCRT, this may be an indication that the person's exertion level is lower than the HR level indicates. The case may be that the person has not fully recovered from a previous exercise. It is inappropriate for the person to exercise at that HR level and this may be indicated to the person.

The references to TCRT low/high may refer to absolute values of TCRT. Alternatively, those references may be indicative of the relationship TCRT/HR. The absolute or relative values may be considered as such or they may be personalized for the person carrying out the fitness exercise. That is, a limit for the TCRT/HR relation may be different for different persons. A reference exercise and/or physiological data of the person may be collected to determine the threshold values.

Although the above refers to HR and TCRT, the embodiments may use other measures as well. Instead of HR, the heart rate parameter may be heart rate variance, for instance. Instead of TCRT, any other vector measure characterizing the relation of the R and T waves in the multidimensional ECG data may be used as well. The method in FIG. 4 may be carried out online. The device(s) carrying out the method may include at least one element of a group comprising a processor usable is an electric device, a performance monitor, a mobile station, an external computer, and an exercise device. Instead of or in addition to the online mode of the method, except for the measurement of the multidimensional ECG data, the method may be applied after the exercise. That is, the ECG data may be stored in a memory from which it may be read and analyzed after the exercise.

Figure 5:
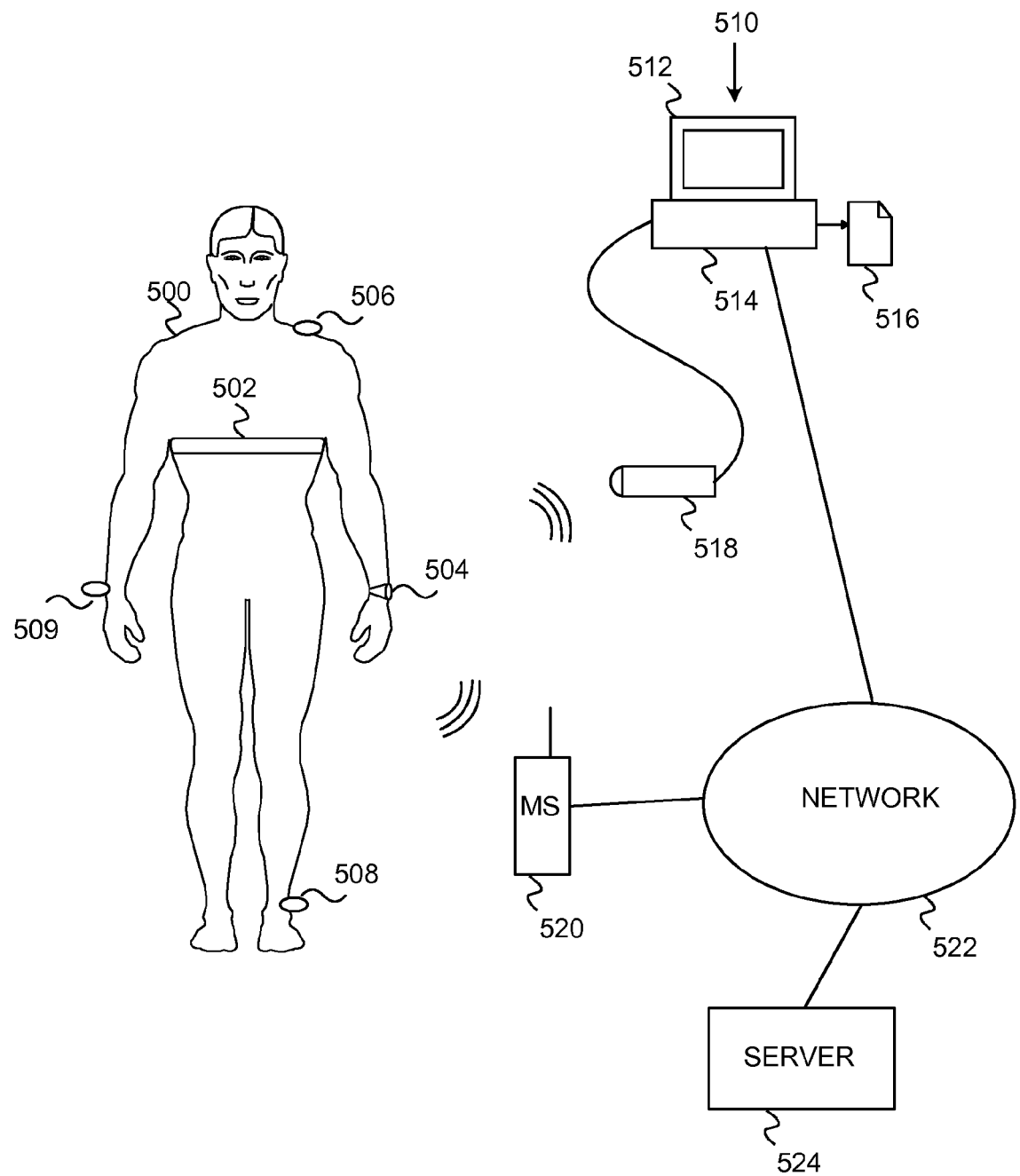
FIG. 5 shows an embodiment of an apparatus.

FIG. 5 shows an embodiment of an apparatus. In the figure, a person 500 who may carry out a fitness exercise is shown. In conjunction with the exercise, a multidimensional ECG may be measured from the person 500. To measure the multidimensional ECG, at least three measuring electrodes are positioned on the person. The at least three electrodes enable ECG measurement on at least two spatially separated couplings. The at least two ECG signal components measured by the coupling may be combined to multidimensional ECG data. The electrode belt 502 may provide some or all of the electrodes. Alternatively or additionally to the electrode belt, some electrodes may be positioned on the back or the shoulder of the person, for instance.

The person may carry a wrist-worn receiver unit 504. Construction of the multidimensional ECG and a vector measure on the basis of the multidimensional ECG may be carried out in the electrode belt or in the receiver unit 504, for instance. The performance monitor may also apply the vectorcardiographic measure in determining a value of a fitness-exercise-related parameter. In an embodiment, instructions relating to the suitability of the exercising level may be provided to the person.

Alternatively to the two-piece performance monitor of FIG. 5 including the electrode belt 502 and the wrist-worn device 504, the functionality may be implemented in a one-piece performance monitor as well. The electrode belt 502 on the chest, for instance, may carry out all the needed functionality.

FIG. 5 also shows an external computer 510, which may receive the heart rate data from the performance monitor. In the heart rate data, the spatially separately measured ECG components may coexist or the data may be in multidimensional ECG format. The data may be received online during the exercise or may be stored during the exercise on the performance monitor and transferred afterwards to the computer 510. Wired or wireless data transmission may be applied between the performance monitor and the computer 510.

The computer 510 may include a display 512, a processing unit 514, a data storage unit 516 and a communication unit 518 for communicating with the performance monitor worn by the user.

If the computer 510 is used in the online mode, it may be operated by a coach of the exercising person, for instance. The computer 510 may plot parameters, such as a value of the vector measure and/or the heart rate of the person on the screen 512. The computer may provide instructions to the coach or the exercising person of how the exercise should be carried on. The instruction may be, for instance, that "the current exercising level is appropriate" or that "the current exercising level is too high". These indications may be provided by the computer or the performance monitor, by using sound and/or visual indication.

The computer 510 in FIG. 5 may be situated in an exercising device, such as a treadmill, for instance. The performance monitor used by the person may in such a case be equipped with communication equipment/functionality to communicate with the treadmill. The instructions to the user may in that case be given by the treadmill or by the performance monitor.

The computer 510 may also be used in a pre-exercise or post-exercise mode. In the pre-exercise mode, the resting heart rate of the person may be compared with the vectorcardiographic measure and a suitable level of the exercise may be determined. In the post-exercise mode, the performance monitor may store the spatially separately measured ECG data during the exercise. The data may be transferred after the exercise to the computer, where it may be analyzed. The analysis may be visual analysis, for instance, where the display of the computer 510 shows analysis of the relationship of the vector measure and the heart rate of the person during the exercise, and draws conclusions on the suitability of the exercise level of the person during the exercise.

FIG. 5 also shows a mobile station 520, which may be wirelessly connected to the performance monitor 504. The mobile station may receive the ECG data from the performance monitor 504 and communicate the data via a data network 522, such as the Internet, to an external server computer 524. Similarly to the computer 510, the server computer 524 may be connected to the performance monitor online or before/after the exercise for controlling and/or monitoring the exercise performed by the person.

In addition or alternatively to the heart rate, some other heart rate parameter, such as heart rate variance, or the activity of the person may be determined. A GPS (Global Positioning System) receiver 506 may receive GPS signals for determining the position of the person 500. Movement of the person may then be determined from the changes in the person's position in time. Movement of the person may also be determined by using a foot pod 508, which calculates the distance walked/run on the basis of the steps taken by the person. Furthermore, an activity monitor 509 may be provided to measure the activity of the person.

Data from one or more of the devices 504, 506, 509 shown may be used to determine the exertion level of the person. This exertion level may be compared to the vector measure and applied in determination of a fitness-exercise-related parameter.

Therefore, it is clear that the embodiments can be carried out in various devices. To list some embodiments provided by FIG. 5, at least the following ones may be identified. All the functionality may be provided in the performance monitor, one-piece or two-piece, online. In another embodiment, the performance monitor is used in a pre-exercise mode to determine a suitable level of exercise. Alternatively, the performance monitor is applied in a post-exercise mode. In such a case, the performance monitor stores the heart rate data during the exercise and provides the functionality to analyze the data afterwards.

The combination of the performance monitor and the external computer 510 and/or the server computer 524 may be applied online or in a post-exercise mode as explained above. Here it may be noted that in an embodiment, the performance monitor used by the person includes only the electrode belt. The electrode belt 502 may measure the ECG signal from the person and send the heart rate information to the computer 510, or to the mobile station 520. The computer 510 or the server 524 may then prepare and provide the control information to control the exercise.

Figure 6:
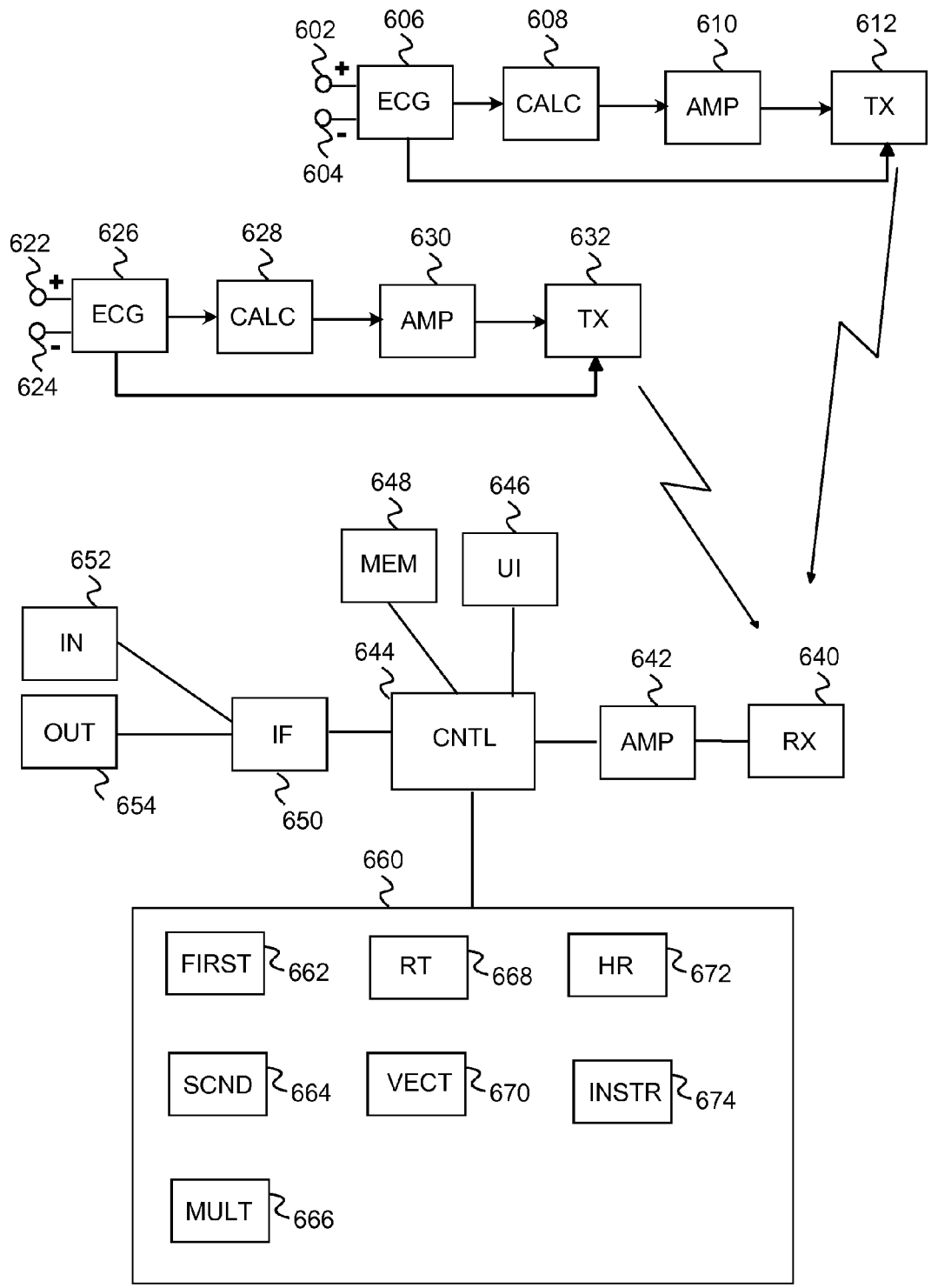
FIG. 6 shows another embodiment of an apparatus.

FIG. 6 shows another embodiment of an apparatus. As will be explained in the following, the apparatus of FIG. 6 may be placed in a single device or distributed over several devices.

The apparatus includes means 602 to 612 for measuring a first ECG component. The electrodes 602, 604 measure a potential difference caused by electrical activation of the person's heart on the person's body. The signal is applied to an ECG preamplifier 606, and may be filtered, after which the heart rate may be calculated. A signal illustrative of the heart rate signal may be amplified in the amplifier 610 before its transmission. FIG. 6 also shows a connecting line from the ECG preamplifier 606 to the transmitter unit 612. That is, the ECG signal may also be transmitted as raw data.

The apparatus also includes second means 622 to 632 for measuring a second ECG component. The functionality of the components 622 to 632 correspond to the respective components 602 to 612. The measurement carried out by the electrodes 622, 624 is spatially separated from the measurement carried out by the electrodes 602 to 604. That is, at least one of the electrodes 622, 624 is different from the electrodes 602 and 604.

The transmitters 612 and 632 may transmit the ECG signal components to a receiver 640. Wired or wireless transmission may be applied in the transmission. The wireless transmission may be inductive or radio transmission, for instance.

The apparatus may include a receiver 640 for receiving the first and second ECG components and/or the associated heart rate data. Identifiers may be associated with each ECG component such that they are identified in the receiver 640.

The signal may be filtered and amplified in the amplifier 642 before forwarding it to a central processor 644, which coordinates the operation of different entities of the receiver.

The device may include a user interface 646. The user interface 646 may include a display for displaying data relevant to operating the device. With regard to a fitness exercise, the display may display the heart rate and/or the heart rate variation of the person, a value of a vectorcardiographic measure and interpretation of the relationship between the heart rate and the vectorcardiographic measure, for instance. The user interface 646 may also include a keyboard. The person may select, by using the keyboard, a mode of the device, in which the vectorcardiographic measure is formed and applied in determining a fitness-exercise-related parameter.

The user interface 646 may further include a sound device. The sound device may provide a sound indication when the person's exercise level is appropriate or needs adjustment.

The device may also include an interface module 650, which may receive data via a receive module 652 or transmit data via a transmit module 654. Via these interface modules 652, 654 the device may communicate with further devices. For instance, if the devices 602 to 654 belong to a wrist-worn performance monitor, the external interfaces may be applied for exchanging data with an external computer, an exercising device, a mobile station or a server computer, for instance.

The device may further include a fitness exercise module 660, which may include following functional entities. A module 662 for processing a first ECG component and a module for processing a second ECG component 664 may be provided. The module 666 may combine the ECG signal components from the modules for processing the first and second ECG components 662, 664 to multidimensional ECG data.

The RT module 668 may extract the R and T wave components from the multidimensional ECG data and form a vector representation of each. Each of the R and T wave components may represent the wave in an orthogonal three-dimensional coordinate system over a time window. The representation may be averaged over time.

The unit 670 forms a vectorcardiographic measure 670 characterizing a relationship between the R and T vectors. The vectorcardiographic measure may be the angle between the R and T vectors, or a TCRT measure, for instance.

A heart rate unit 672 may calculate the heart rate of the user by using one or more of the ECG components.

The instruction module 674 may provide instructions to be given to the user for carrying out the exercise. The instructions may be formed on the basis of the vectorcardiographic measure alone or the vectorcardiographic measure and the heart rate together. A lookup table or a calculation algorithm may be used to determine the appropriate instruction.

With regard to the device implementation, several alternatives exist for FIG. 6.

In an embodiment, all the functionality is in an electrode belt.

In another embodiment, the functionality is distributed between the electrode belt and the wrist-worn device of the performance monitor. The electrode belt may transmit the ECG components to the wrist-worn device, which may be responsible for further processing of the data. Alternatively, the electrode belt may form the multidimensional ECG data and transmit it to the wrist-worn device for further processing. Alternatively, the electrode belt may form the vector measure, and transmit information thereon to the wrist-worn device for applying in controlling the exercise.

Alternatively, the functionality may be distributed over even more devices. For instance, the data of the ECG components may directly be transmitted to an external device from the performance monitor. Thus, further processing of the ECG component data may be carried out in an external computer, an exercising device or a server computer, for instance.

A method and a computer program product implementing the method and carrying out the functionality of the apparatus may be provided. The embodiments may be implemented by software, hardware, or a combination thereof. The embodiments may be implemented on one or more devices including a processor, a performance monitor, a mobile station, a computer or an exercise device, for instance.

The disclosed functionality in various embodiments may be implemented by way of a computer program product encoding a computer program of instructions for executing a computer process of the above-described method. The computer program product may be implemented on a computer program distribution medium. The computer program distribution medium may be any of the known ways of distributing software, such as a computer readable medium, a program storage medium, a record medium, a computer readable memory, a computer readable software distribution package, a computer readable signal, a computer readable telecommunication signal, and a computer readable compressed software package. Alternatively, part of the functionality may be implemented by hardware, such as ASIC (Application Specific Integrated Circuit) or by a combination of hardware and software.

It will be obvious to a person skilled in the art that, as the technology advances, the inventive concept can be implemented in various ways. The invention and its embodiments are not limited to the examples described above but may vary within the scope of the claims.

What is claimed is:

1. An apparatus in connection with a fitness exercise of a person, the apparatus comprising:
    a processing device to process multidimensional electrocardiographic data of the person, the multidimensional electrocardiographic data comprising at least two spatially separately measured electrocardiographic signal components obtained by using two couplings of electrodes and a total of at least three electrodes, each of the couplings of electrodes including two electrodes;
    a forming device to form a vectorcardiographic measure on the basis of the multidimensional electrocardiographic data;
    an applicator to apply the vectorcardiographic measure and a heart rate parameter to determine a fitness-exercise-related parameter; and
    an instruction module to provide exercise instructions from the fitness-exercise-related parameter, the exercise instructions to be given with a user interface to the person for carrying out the fitness exercise, wherein the instruction module applies a lookup table or a calculation algorithm to determine the exercise instructions from a variety of exercise instructions.

2. The apparatus of claim 1, wherein the apparatus further comprises a transformer to transform at least a portion of the multidimensional electrocardiographic data into an orthogonal representation of the data having three mutually different directions that are not all in the same plane.

3. The apparatus of claim 1, wherein the apparatus comprises:
    a monitoring device to monitor a heart rate of the person; and
    a determiner to determine the fitness-exercise-related parameter on the basis of the heart rate of the person and the vectorcardiographic measure.

4. The apparatus of claim 1, wherein the apparatus further comprises:
    an identifier to identify a multidimensional R wave and a multidimensional T wave from the multidimensional electrocardiographic data; and
    a forming device to measure, as the vectorcardiographic measure, a relationship between the multidimensional R wave and the multidimensional T wave.

5. The apparatus of claim 1, wherein the apparatus comprises:
    a forming device to form a vector representation of a multidimensional R wave in the electrocardiographic data;
    a forming device to form a vector representation of a multidimensional T wave in the electrocardiographic data; and
    an estimator to estimate an angle measure of the angle between the vector representation of the multidimensional R wave and the vector representation of the multidimensional T wave.

6. The apparatus of claim 1, wherein the apparatus further comprises:
    a monitoring device to monitor if the vectorcardiographic measure exceeds a predetermined threshold value; and
    an indicator to indicate if the vectorcardiographic measure exceeds a predetermined threshold value.

7. The apparatus of claim 1, wherein the applicator applies the vectorcardiographic measure to determine the fitness-exercise-related parameter during the fitness exercise and/or after the fitness exercise.

8. The apparatus of claim 1 wherein the processing device comprises at least one element of a group consisting of: a processor usable as an electric device, a performance monitor, a mobile station, an external computer and an exercise device.

9. The apparatus of claim 1 wherein the fitness-exercise-related parameter comprises at least one element of a group consisting of: exertion level of the person associated with the fitness exercise, mental stress, and energy expenditure.

10. The apparatus of claim 1, wherein the apparatus comprises an operation mode, in which the processing device processes multidimensional electrocardiographic data of the person, the forming device forms a vectorcardiographic measure of the multidimensional electrocardiographic data, and the applicator applies the vectorcardiographic measure to determine the fitness-exercise-related.

11. The apparatus of claim 1, wherein the applicator applies the vectorcardiographic measure to determine the fitness-exercise-related parameter before the fitness exercise.

12. The apparatus of claim 1, wherein the exercise instructions comprise an indication of a level at which the fitness exercise can be started or continued.

13. The apparatus of claim 1, wherein the heart rate parameter is a heart rate or a heart rate variation.

14. A computer program product embodied in a non-transitory distribution medium readable by a computer and comprising program instructions which, when executed by an apparatus, perform operations comprising:
    processing multidimensional electrocardiographic data of a person, the multidimensional electrocardiographic data comprising at least two spatially separately measured electrocardiographic signal components obtained by using two couplings of electrodes and a total of at least three electrodes, each of the couplings of electrodes including two electrodes;
    forming a vectorcardiographic measure on the basis of the multidimensional electrocardiographic data;
    applying the vectorcardiographic measure and a heart rate parameter to determine a fitness-exercise-related parameter; and
    providing exercise instructions from the fitness-exercise-related parameter, the exercise instructions to be given with a user interface to the person for carrying out a fitness exercise, wherein the exercise instructions are determined from a variety of exercise instructions by using a lookup table or a calculation algorithm.

15. The computer program product of claim 14, wherein the operations further comprise:
    transforming at least a portion of the multidimensional electrocardiographic data into an orthogonal representation of the data having three mutually different directions that are not all in the same plane.

16. The computer program product of claim 14, wherein the operations further comprise:
    identifying a multidimensional R wave and a multidimensional T wave from the multidimensional electrocardiographic data; and measuring, as the vectorcardiographic measure, a relationship between the multidimensional R wave and the multidimensional T wave.

17. The computer program product of claim 14, wherein the operations further comprise:
   forming a vector representation of a multidimensional R wave in the electrocardiographic data;
   forming a vector representation of a multidimensional T wave in the electrocardiographic data; and
   estimating an angle measure of the angle between the vector representation of the multidimensional R wave and the vector representation of the multidimensional T wave.

18. The computer program product of claim 14, wherein the operations further comprise:
   monitoring if the vectorcardiographic measure exceeds a predetermined threshold value; and
   indicating if the vectorcardiographic measure exceeds a predetermined threshold value.

19. An apparatus in connection with a fitness exercise of a person, the apparatus comprising:
   a processing device to process multidimensional electrocardiographic data of the person, the multidimensional electrocardiographic data comprising at least two spatially separately measured electrocardiographic signal components obtained by using two couplings of electrodes and a total of at least three electrodes, each of the couplings of electrodes including two electrodes;
   a forming device to form a vectorcardiographic measure on the basis of the multidimensional electrocardiographic data;
   a processing device to process activity data of the person, the activity data representing activity of the person and obtained by using at least one motion tracking device worn during the fitness exercise;
   a determining device to determine exertion level of the person on the basis of the activity data; and
   a comparing device to compare the exertion level of the person and the vectorcardiographic measure in order to provide an indication of what at least partly causes the vectorcardiographic measure of the person.

20. The apparatus of claim 19, further comprising:
   an applicator to apply the vectorcardiographic measure and the exertion level of the person to determine a fitness-exercise-related parameter.

21. The apparatus of claim 19, wherein the motion tracking device worn during the fitness exercise is selected from the group of tracking devices consisting of at least one of: a global positioning system receiver, a foot pod, and an activity monitor.

* * * * *